(12) United States Patent
Herrera-Estrella et al.

(10) Patent No.: US 7,670,830 B2
(45) Date of Patent: Mar. 2, 2010

(54) TRICHODERMA SPP STRAINS WITH HIGH CAPACITY OF FUNGUS BIOLOGICAL CONTROL AND SELECTION PROCESS THEREOF BY MOLECULAR MARKERS

(75) Inventors: Alfredo Heriberto Herrera-Estrella, Irapuato (MX); Rafael Eduardo Galdames-Gutierrez, Temuco (CL); Jose Pedro Martinez-Hernandez, Salamanca (MX)

(73) Assignee: Cosmocel, SA, San Nicolas de los Garza, Nuevo Leon (MX)

( * ) Notice: Subject to any disclaimer, the term of this patent is extended or adjusted under 35 U.S.C. 154(b) by 732 days.

(21) Appl. No.: 11/244,089

(22) Filed: Oct. 6, 2005

(65) Prior Publication Data

US 2006/0034806 A1    Feb. 16, 2006

Related U.S. Application Data

(62) Division of application No. 10/371,202, filed on Feb. 24, 2003, now abandoned.

(30) Foreign Application Priority Data

Jul. 4, 2002    (MX) .................. PA/A/2002/006678

(51) Int. Cl.
*C12N 1/14*    (2006.01)
(52) U.S. Cl. .................. 435/254.6; 424/93.5; 424/254.1
(58) Field of Classification Search .................. None
See application file for complete search history.

(56) References Cited

U.S. PATENT DOCUMENTS

| | | | | |
|---|---|---|---|---|
| 4,489,161 A | * | 12/1984 | Papavizas | 435/256.7 |
| 4,668,512 A | * | 5/1987 | Lewis et al. | 424/93.5 |
| 4,713,342 A | * | 12/1987 | Chet et al. | 424/93.5 |
| 4,748,021 A | * | 5/1988 | Chet et al. | 424/93.5 |
| 5,238,690 A | * | 8/1993 | Elad et al. | 424/93.5 |

OTHER PUBLICATIONS

Lo et al., Plant Diseases, vol. 80, pp. 736-741.*
Dennis and Webster, *Antagonistic Properties of Species-Groups of Trichoderma*. Trans. Brit. Mycol. Soc. 1971. 57(1), 25-39.
Dennis and Webster, *Antagonistic Properties of Species-Groups of Trichoderma*. Trans. Brit. Mycol. Soc. 1971. 57(1), 41-48.
Elad, et al. *Degradation of Plant Pathogenic Fungi by Trichoderma harzianum*. Can. J. Microbiol. 1982, 28:719-725.
Chet. *Trichoderma Application, Mode Of Action, And Potential As A Biocontrol Agent Of Soilborne Plant Pathogenic Fungi*. New York: Wiley & Sons. 137-160. b.w. 1987.
Herrera-Estrella and Chet. *Biocontrol of Bacteria and Phytopathogenic Fungi*. Agricultural Biotechnology. Arie Altman Ed. Marcel Dekker, Inc. New York, NY USA pp. 263-282, 1988.

* cited by examiner

*Primary Examiner*—Irene Marx
(74) *Attorney, Agent, or Firm*—Browdy and Neimark, PLLC

(57) ABSTRACT

*Trichoderma* spp. strains with high capacity for fungus biological control in wide ranges of temperature and pH are described, such strains being compatible with each other. Likewise, a process of selection of such strains through molecular markers is described. The described process reduce the number of necessary experiments to determine if a *Trichoderma* strain, not previously described, can display a biological activity more acceptable than those well known.

6 Claims, 5 Drawing Sheets

CIEAV-30   CIEAV-40                    CIEAV-62

TRICHODERMA SPP STRAINS WITH HIGH CAPACITY OF FUNGUS BIOLOGICAL CONTROL AND SELECTION PROCESS THEREOF BY MOLECULAR MARKERS

FIELD OF THE INVENTION

The present invention refers to techniques for fungus biological control and, more specifically, it refers to *Trichoderma* spp. strains with high capacity of fungus biological control and a process for selection thereof by molecular markers.

BACKGROUND OF THE INVENTION

Survival of agricultural cultivates during its development, in the face of multiple pathogenic agents attacking them, is due principally to the natural existence of biological control. Several microorganisms capable of antagonizing the effect of other phytopathogenic microorganisms give this control.

Development and application of this natural potential is becoming more and more important as man has become able to participate and improve it and, will almost certainly have a big impact in agriculture in the near future, since the use of biological control agents in the country is an important factor in reducing chemical pesticides and therefore pollution, caused thereby.

In general, the microorganisms used in biological control are originated from isolates carried out from soil. However, not all isolated microorganisms present optimal characteristics for its use in biological control.

In this respect, the studies about behavior of these agents in different pH and weather condition and with several different microbial communities are very rare. However, some microorganisms have been accepted as biological control agents, as is the case of fungus belonging to the *Trichoderma* genus. As hyperparasites these active organisms have been proved extensively in field experiments, where it has been demonstrated that they can be effective as biological control agents against a very wide range of pathogens both air borne as soil borne, as it was described by Herrera-Estrella and Chet in 1998 ("Agricultural Biotechnology", Arie Altman Ed. Marcel Dekker, Inc. New York, N.Y. USA pp. 263-282).

Likewise, several different factors have been identified as being involved in growth inhibition and/or pathogenic fungus destruction by *Trichoderma*, in which antibiotics and cell wall hydrolytic enzymes are found, besides to direct physical interaction that include winding over the host's hyphes and specialized structures formation of apprehensive type, as described in several references as above by Herrera-Estrella and Chet, or else, other references as that by Chet in 1987 (Ed. I. Chet, New York: Wiley & Sons. 137-160. b w), Dennis and Webster in 1971 (Trans. Brit. Mycol. Soc. 57: 41-48 and Trans. Brit. Mycol. Soc. 57: 25-39) and that of Elad, Chet and Henis in 1982 (Can. J. Microbiol. 28: 719-725).

Current Knowledge and techniques allow planning of use of improved strains of *Trichoderma* as an alternative in pathogenic fungus control in the country. However, up to date it has not been possible to carry out a largely effective and productive biological control, since no selection from suitable isolate or strain at country and weather conditions prevailing at the place where they are to be used has been carried out, so as according to the pathogen(s) agent(s)-object. The fact that no strain nor isolate can be considered of universal utility for control of all kinds of pathogens and all kinds of environmental conditions, makes that, despite the great development the use of these microorganisms have had in biological control, up to date it has not been possible to use them in the best manner, since in some cases the growth of the control agent is not enough, or basically it can not control all present pathogenic agents. Furthermore, when mixtures of strains or *Trichoderma* species are used to try to control different biologically pathogens, in some cases they inhibit each other creating a poorer biological control, instead of the improvement desired.

On the other hand, development of molecular genetic markers has opened doors for an intensive research and genetic characterization of many organisms such as bacteria, plants, fungus and insects. Such molecular markers allow collection and use of information of microorganisms of natural occurrence, in other words, carrying neutral phenotypicaly polymorphism within a population. The majority of the populations have relatively high frequency of such polymorphism, as they can be due to slight changes at DNA level such as base changes, insertions, deletions and translocations.

As a consequence thereof, it has been looked to abolish the inconveniences found in the use of the same *Trichoderma* strains for biological control of pathogenic fungus in the country, independently of environmental and weather conditions, through the development of a process that assisted by the use of molecular genetic markers, would allow the selection of *Trichoderma* strains having an optimal performance for biological control of certain specific pathogens of interest and at environmental conditions to which they will be subjected to at the country.

OBJECTS OF THE INVENTION

An object of the present invention is to provide *Trichoderma* spp. strains with high capacity for fungus biological control in wide ranges of temperature and pH.

An object of the present invention is to provide *Trichoderma* spp. strains with high capacity for fungus biological control, which are compatible with other *Trichoderma* strains.

An object of the present invention is to provide a process for the selection of *Trichoderma* spp. strains having high capacity for fungus biological control through molecular markers, which allow to obtain *Trichoderma* spp. strains which can produce an optimal biological control at different temperature and pH conditions.

An object of the present invention is to provide a process for the selection of *Trichoderma* spp. strains with high capacity for fungus biological control through molecular markers, which allow to obtain *Trichoderma* spp. strains which can produce an optimal biological control of a great diversity of pathogenic agents.

An object of the present invention is to provide a process for the selection of *Trichoderma* spp. strains with high capacity for fungus biological control through molecular markers, which allow to reduce the number of necessary experiments to determine if a *Trichoderma* strain, not previously described, can display a biological activity more accepted than those well known.

BRIEF DESCRIPTION OF THE DRAWINGS

The novel aspects that are considered characteristics of the present invention will be settled in detail in the attached claims. However, the operation, along with other objects and advantages thereof, will be better understood in the following detailed description of a specific embodiment when it is read in relation to following figures:

FIG. 2 is a photograph of the results from the molecular-genetic markers detection step of a preferred embodiment of the process of the present invention for strains obtained in the in vitro growth rate measurement step.

FIG. 3A is a bottom view of the results of the confrontation step with in vitro pathogens for CIEAV-40, CIEAV-55 and CIEAV-30 strains of a preferred embodiment of the present invention process.

FIG. 3B is a top view of the results of the confrontation step with in vitro pathogens for CIEAV-40, CIEAV-55 and CIEAV-30 strains of a preferred embodiment of the present invention process.

FIG. 4 is a top view of the results of a preferred embodiment of the in vitro growth measurement step of pathogens in the presence of secreted or excreted substances from identified strains in the molecular-genetic markers detection step for R. Solani in the culture medium where the substances produced by CIEAV-62 and CIEAV-52 are found.

DETAILED DESCRIPTION OF THE INVENTION

It has been found that by the use of molecular biology techniques it is possible to carry out, from a collection of natural strains, a process that allows the selection of Trichoderma strains with high capacity of biological control in a wide range of phytopathogenic fungus under several different environmental conditions.

Through the process that will be later described, it was possible to obtain CIEAV-30, CIEAV-40 and CIEAV-62 strains, which satisfy the objects of the present invention in presenting a good growth at variable pH and temperature conditions, also presenting a suitable biological control for a great number of pathogens. For this reason, such strains were deposited at the ATCC (American Type Culture Collection) as International Deposit Authority of the Budapest Treaty for International Recognition of Microorganisms Deposit for Purposes of Patent Proceedings, with numbers PTA-3950 for CIEAV-30 strain, PTA-3951 for CIEAV-40 strain and PTA-3952 for CIEAV-62 strain.

Figure 1:
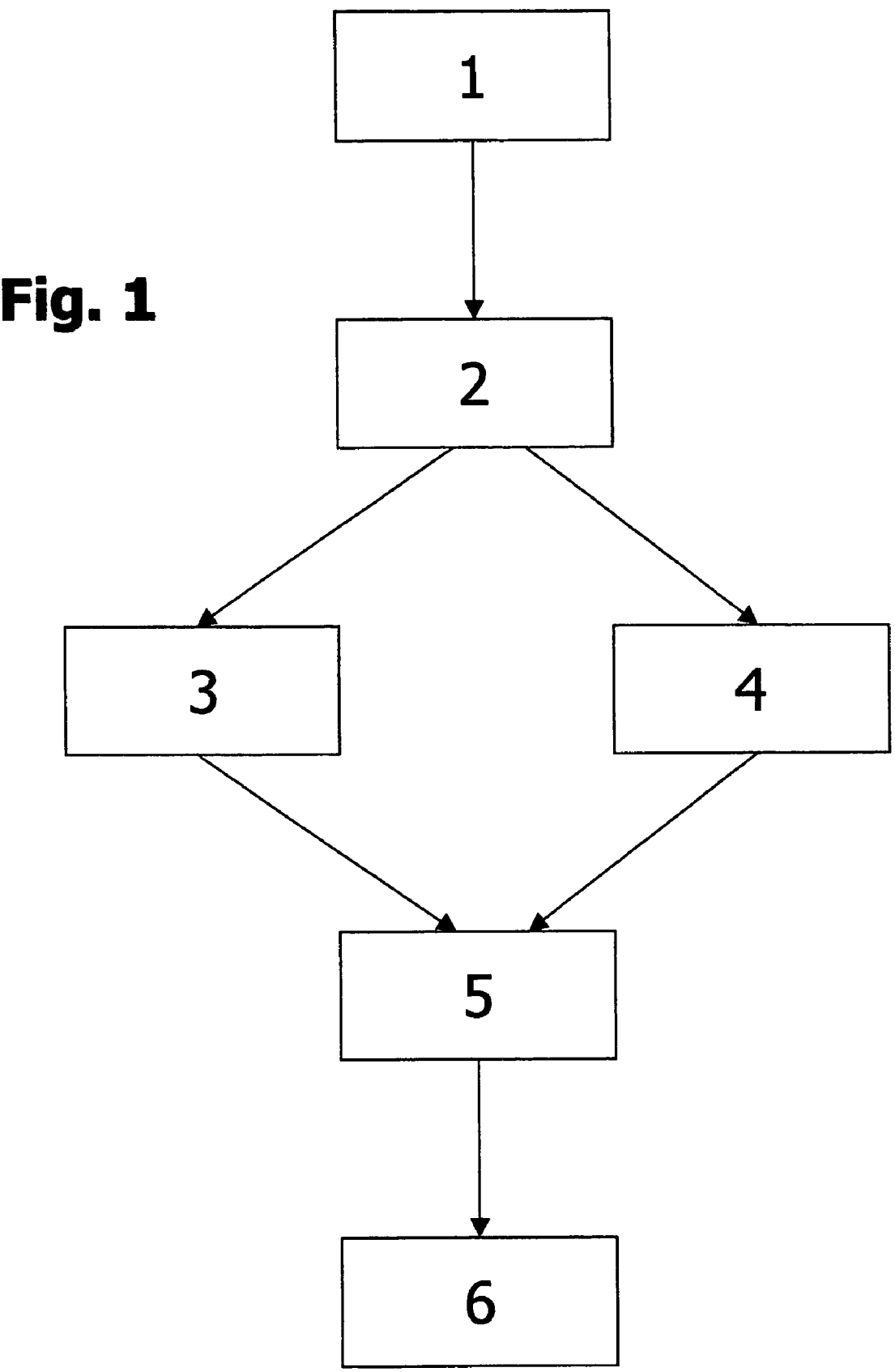
FIG. 1 is a block diagram of a preferred embodiment of the process for the selection of *Trichoderma* spp. strains with high capacity for fungus biological control through molecular markers of the present invention.

With reference to FIG. 1 attached, the process of selection of the present invention comprises the following steps:

a) Step 1: measurement of in vitro growth rates from each strain of a Trichoderma strains collection under diverse pH and temperature conditions in which strains with better growth rates under different pH and temperature tested conditions are identified;

b) Step 2: molecular-genetic markers detection in which genetically different groups are identified from strains selected in the growth rate measurement step, being those strains displaying similar patterns of molecular-genetic markers located in the same group;

c) Step 3: in vitro confrontation with pathogens, in which strains of the diverse groups genetically different identified in the step of molecular-genetic markers, are confronted with a great number of pathogens, using for this various strains, patovars and/or races of each pathogen, identifying the strains that allow a more effective biological control at 60% with respect to the total number of strains, patovars and/or races of the corresponding pathogen that were confronted;

d) Step 4: in vitro measurement of pathogens' growth in the presence of secreted substances from strains identified in the molecular-genetic markers detection step, in which strains that display a lower pathogen growth speed in the presence of substances secreted by such strains are identified; and, e) Step 5: measurement in planta of the performance of the strains identified in the in vitro measurement step of pathogens' growth in which strains that display a better biological control are identified on the settlement and/or the disease progress in planta through greenhouse assays with plants susceptible to pathogen.

In an additional embodiment of the present invention in which it is desired to know if it is possible to produce mixtures from two or more Trichoderma strains. It is also carried out a step 6 of in vitro measurement of compatibility in strains of interest that is accomplished in the same way as the confrontation step with pathogens, but testing instead of the pathogen, the Trichoderma strain or strains to be combined.

The strains identified through the present invention process display an optimal biological control when used in the country, inasmuch as they have the capability to control the great number of variants of pathogens in wide ranges of pH and temperature.

Furthermore, once accomplished the present invention process for a certain Trichoderma strain collection by the step 2 of molecular-genetic markers detection, it is possible to determine for a strain that is incorporated to the collection if it is possible to have a better performance in relation to those already in the collection, since only those strains genotypically different, independent to genotypes already detected, will give raise to better performances.

In the preferred embodiment of the present invention, step 1 of growth rates measurement is preferably carried out by growing Trichoderma strains in vitro in suitable culture medium, preferably potato-dextrose-agar, under acidity or alkalinity conditions, preferably at pH values between 5 and 9, and in the temperature range of interest, preferably between 15 and 40° C., measuring the radial growth speed of the strains. In a specific embodiment of present invention, the culture for the measurement of growth rates step is accomplished adjusting the pH to the required value without a buffer, so medium acidification by the microorganism is possible, as would happen in its normal growth environment.

Likewise, in the described embodiment, the molecular-genetic markers detection step is accomplished through the use of well known markers in the previous art, preferably selected between polymorphism of restriction fragment length "RFLPs"; amplified fragment length polymorphism "AFLPs"; random amplified polymorphic DNA "RAPDs"; microsatellites amplification; or combinations thereof. The strains groups belonging to the same group are formed preferably as described by Skroch, Tivang and Nienhuis described in 1992 (Genetic relations analysis using RADP markers data, pp. 26-30. Symposia Culture Collection of Plants of American Culture Society, American Horticulture Science Society and American Genetic Society, Minneapolis, Minn.) and by Sneath and SOCAL in 1973 (Numeric Taxonomy W. H. Freeman and Co., San Francisco).

As referred to step 3 of confrontation with pathogens in vitro, this embodiment is accomplished preferably in Petri dishes with potato-dextrose-agar, determining if the strain provides or not a suitable biological control through the evaluation of strain over-growth against the growth of pathogen, the appearance of a brown to dark brown coloration on the agar noticed at the bottom of the Petri dish show phenolic compounds production through cellular death, as well as the appearance of a light green to dark green coloration representing the strain capacity to produce spores over the pathogen. In a specific embodiment of step 3 of confrontation with pathogens, an arbitrary range is used to evaluate the over-growth capacity, brown coloration and sporulation, preferably according to tables I, II and III that are shown below:

TABLE I

Evaluation Range (values between 0 and 3) of *Trichoderma* Strains Over-Growth in the Confrontation Step with the Pathogen

| OVER-GROWTH | VALUE |
|---|---|
| HIGH (75-100%) | 3 |
| MEDIUM (50-75%) | 2 |
| LOW (25-50%) | 1 |
| NULL | 0 |

TABLE II

Evaluation Range (Values Between 0 and 2) of Pigmentation Brown to Dark Brown in the Confrontation Step with the Pathogen

| PIGMENTATION | VALUE |
|---|---|
| STRONG | 2 |
| MODERATE | 1 |
| NULL | 0 |

TABLE III

Evaluation Range (Values between 0 and 1) of Sporulation Appearance in the Confrontation Step with the Pathogen

| SPORULATION | VALUE |
|---|---|
| PRESENT | 1 |
| ABSENT | 0 |

According to the preceding data, in the preferred embodiment of the present invention it has been considered that a strain display good biological control of a certain pathogen if the strain display an over-growth of at least 2, a pigmentation of at least 1 and a sporulation of 1 when the confrontation step with pathogens is done.

Now then, according to step 4 of in vitro measurement of pathogens' growth in presence of substances secreted by the strains, in the described embodiment, this step is accomplished by growing of the strain to be tested, preferably in Petri dishes in culture medium of potato-dextrose-agar at 27° C., inoculating an agar fragment of the frontal part of the strain radial growth that is tested on a porous membrane, preferably nylon, in fresh medium, taking off the strain from Petri dish by removing of the porous membrane and inoculating in the same Petri dish the pathogen of interest, finally determining the radial growth speed of the pathogen, which is a measure of the effect from secreted or excreted substances by the strain over the phytopathogen.

Next an example is appointed to clearly illustrate the process of the present invention, which would not be considered as limiting thereof.

EXAMPLE

A collection of seventy-seven *Trichoderma* spp. strains identified as CIEAV-1 and CIEAV-77 was subjected to step 1 of growth rates measurement, which was done by growing the strains in Petri dishes with potato-dextrose-agar at pH conditions of 5, 6, 7, 8 and 9 at a temperature of 27° C. Likewise, the seventy-seven strains were growing at a pH of 5.6 at temperatures of 20, 27 and 37° C. Once the growing were accomplished, 32 strains that display the best average growth rates were identified.

Figure 2:
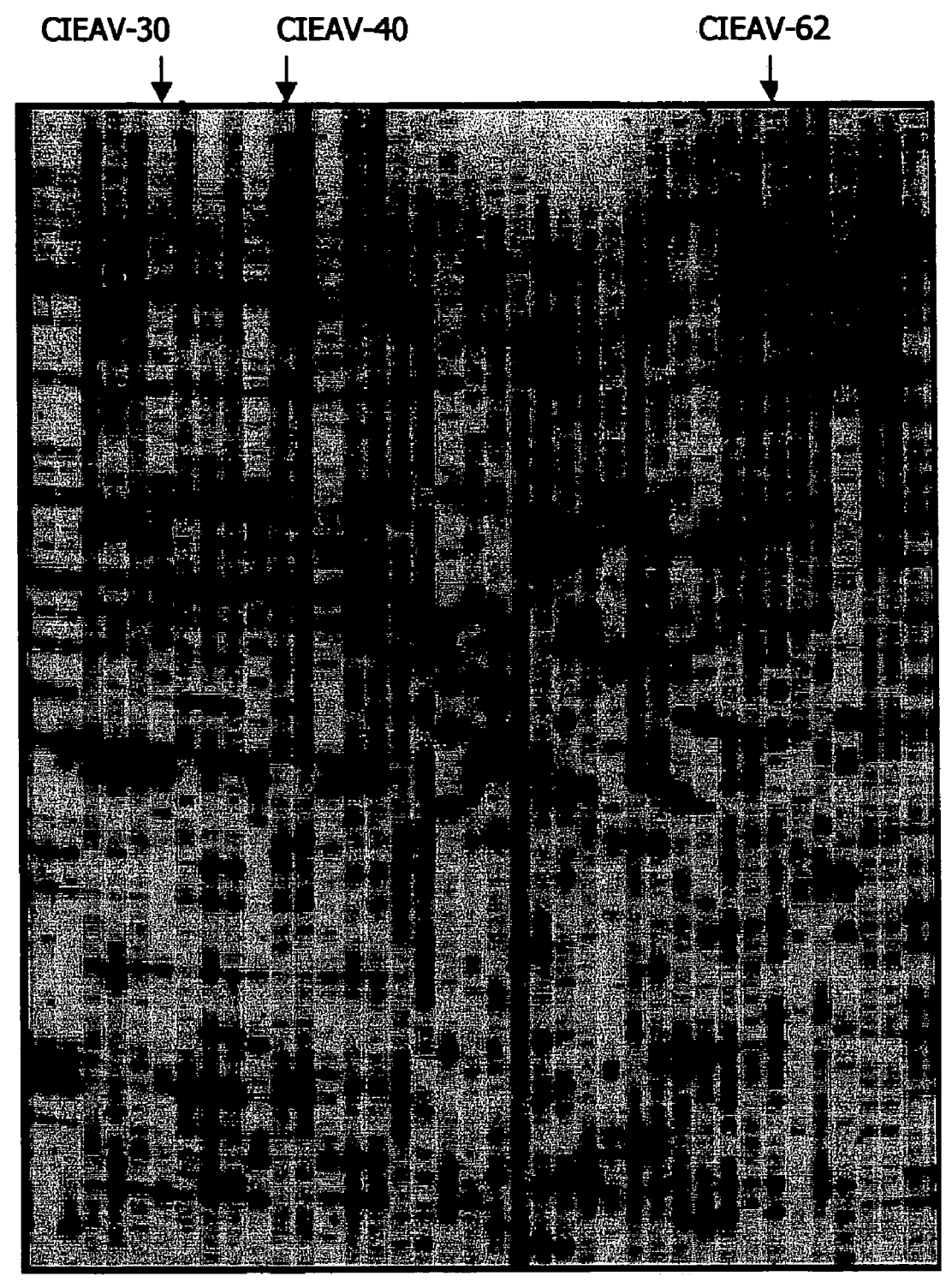

The 32 identified strains were subjected to step 2 of molecular-genetic markers detection step, by an AFLP analysis from which dendograms of genetic distance were constructed. For this, primers EcoRI 5'AGACTGCGTAC-CAATTC-3' (SEQ ID NO:1) and MseI 5'GACGATGAGTCCTGAGTAA-3' (SEQ ID NO:2) were used with an additional nucleotide (EcoRI+A and MseI+A) for pre-amplification. Likewise, to obtain a suitable number of additional bands for analysis, primers with two additional selective nucleotides were used (EcoRI+AA, +AC, +AG o +AT/MseI+AA, +AC, +AG, o +AT) on second amplification. In FIG. 2 an autoradiography AFLP obtained with the pair +AT for 32 strains is shown. The stripes generated in AFLP autoradiography were shown, assigning to stripes (1) in case of presence or (0) in case of absence of reference stripe. Genetic similarity was esteemed according to proportion of coincident stripes (0 and 0 or 1 and 1) between strains' fingerprints, as described by Skroch et al., (previously refereed) and Sneath and Socal (previously referred).

Figure 5:
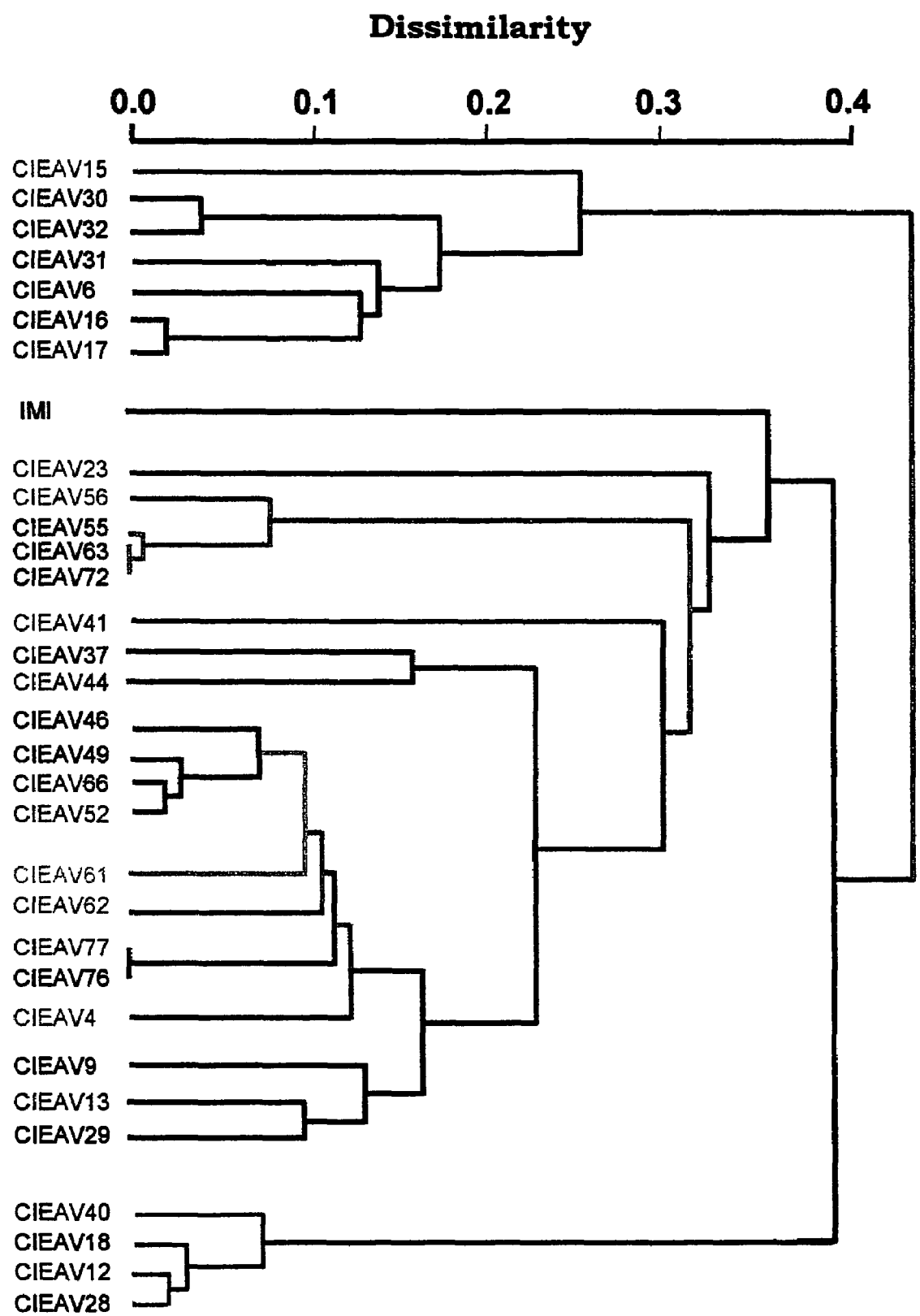
FIG. 5 is a dendrogram generated by the AFLP method from Trichoderma natural strains according to a preferred embodiment of the molecular-genetic markers detection step of the present invention process.

The obtained similarity matrix was used to produce a dendogram, showed in FIG. 5, by unweighted pair group method with arithmetic mean method (UPMGA) as described by Skroch et al., (previously referred) and Sneath and Socal (previously referred). From this analysis 16 strains were identified belonging to genetically independent groups from the 32 analyzed, which were subjected to step 3 of confrontation with pathogens.

The pathogens used were 12 *Fusarium* spp. strains, one *Fusarium solani* strain, one *Fusarium moniliforme* strain, three *Fusarium oxyporum* strains, 16 *Rhizoctonia* spp. strains, 20 *Rhizoctonia solani* strains, one *Colletotrichum gloeosporiodes* strain, 4 *Colletotrichum* spp. strains, 3 *Phytopthora capsici* strains, one *Phytopthora citricola* strain, one *Phytopthora cinammomi* strain and one *Botrytis cinerea* strain.

The percentage of pathogens for which each strain was effective, in other words, which presented a higher than 2 over-growth, brown to dark brown coloration higher than 1 and sporulation of 1, are presented in table 4.

TABLE 4

Effectivity of Selected Strains in Molecular-Genetic Markers Detection Step against Different Pathogens

| Trichoderma sp. | Fusarium sp. | Rhizoctonia sp. | Phytophtora sp. | Botrytis cinerea | Colletotrichum sp. |
|---|---|---|---|---|---|
| CIEAV-4 | 16.66% | 25% | 40% | 0% | 20% |
| CIEAV-12 | 5.55% | 8.33% | 40% | 0% | 40% |
| CIEAV-13 | 5.55% | 61.1% | 60% | 0% | 0% |
| CIEAV-15 | 27.7% | 52.77% | 40% | 0% | 40% |
| CIEAV-17 | 38.88% | 58.33% | 20% | 0% | 20% |
| CIEAV-23 | 11.11% | 50% | 80% | 0% | 20% |
| CIEAV-30 | 66.66% | 72.22% | 80% | 100% | 60% |
| CIEAV-40 | 94.44% | 91.66% | 100% | 100% | 100% |
| CIEAV-41 | 33.33% | 77.77% | 80% | 100% | 80% |
| CIEAV-44 | 0% | 25% | 40% | 100% | 20% |
| CIEAV-52 | 66.66% | 8.33% | 0% | 0% | 20% |
| CIEAV-55 | 0% | 8.33% | 60% | 0% | 60% |
| CIEAV-56 | 11.11% | 16.67% | 60% | 0% | 40% |
| CIEAV-61 | 11.11% | 19.44% | 40% | 0% | 0% |

TABLE 4-continued

Effectivity of Selected Strains in Molecular-Genetic Markers Detection Step against Different Pathogens

| Trichoderma sp. | Fusarium sp. | Rhizoctonia sp. | Phytophtora sp. | Botrytis cinerea | Colleto- trichum sp. |
|---|---|---|---|---|---|
| CIEAV-63 | 0% | 2.77% | 60% | 0% | 0% |
| CIEAV-62 | 83.33% | 47.22% | 20% | 100% | 20% |
| CIEAV-66 | 11.11% | 52.7% | 80% | 100% | 60% |
| CIEAV-77 | 16.67% | 2.77% | 20% | 0% | 20% |
| Control 1 | 22.22% | 44.44% | 20% | 0% | 40% |
| Control 2 | 61.11% | 66.66% | 80% | 100% | 60% |

With the aim of having a reference parameter of antagonistic activity, strains IMI206040 from *T. Atroviridae* (Control 1) and T35 from *T. Harzianum* (Control 2) were used as controls.

Figures 3A, 3B:
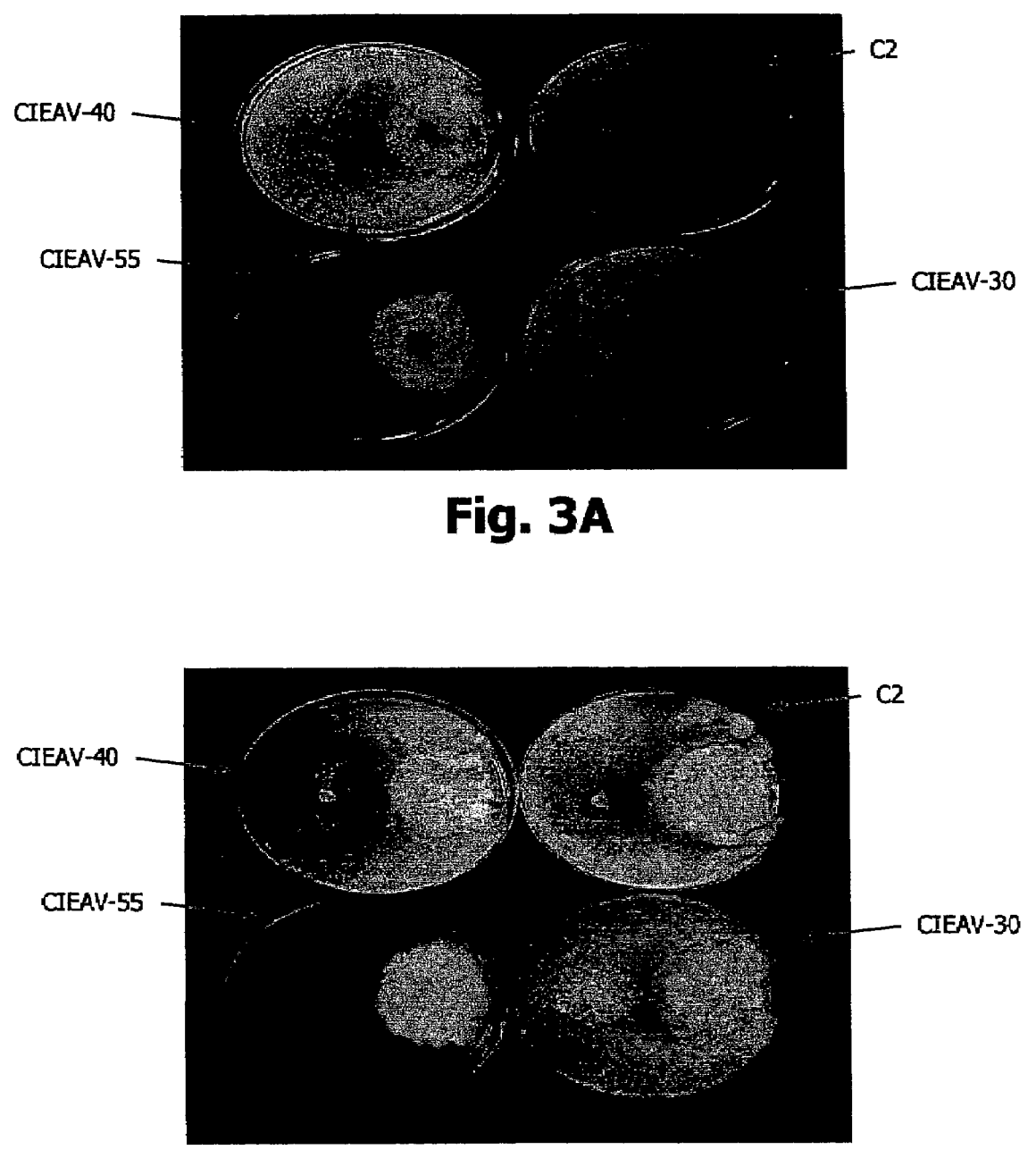

In FIGS. 3A and 3B top and bottom views of an in vitro assay from strains CIEAV-40, strain T35 from *T. Harzianum* as control (C2), CIEAV-55 and CIEAV-30 are presented respectively with *Rhizoctonia solani*.

Likewise, 32 strains selected from molecular-genetic markers detection step were subjected to step 5 of in vitro measurement of *R. solani* growth as indicator pathogen in the presence of secreted or excreted substances from such stains, in which these assays determine radial growth speed of indicator colony. According to this analysis, substances produced by stain CIEAV-62 in a great majority inhibited completely the indicator growth, and as a consequence, were submitted for its deposit with the ATCC.

Figure 4:
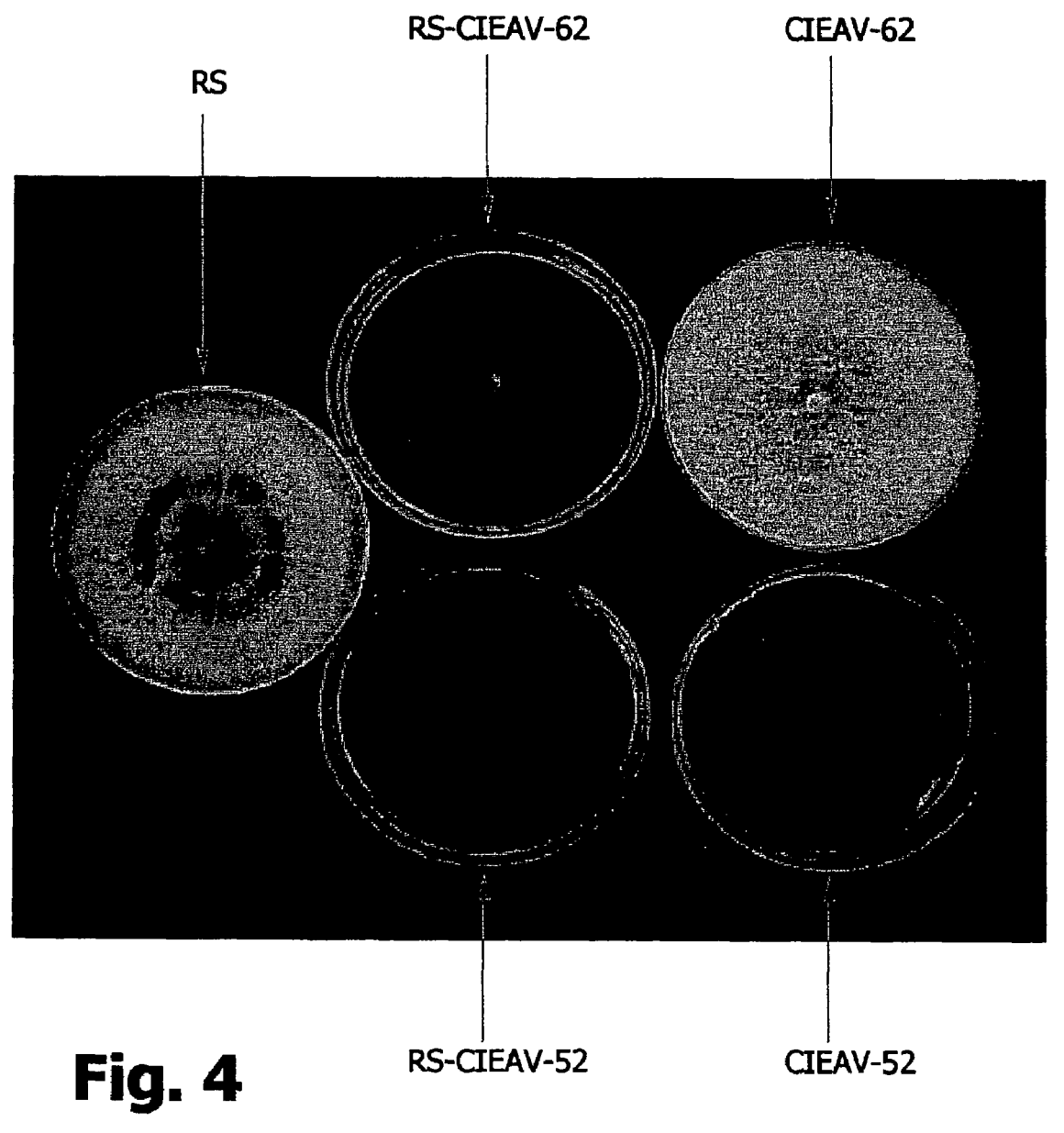

In FIG. 4 an example of this test is shown, in which the growth of *Rhizoctonia solani* alone (RS) as a control can be seen, of *Rhizoctonia solani* grown over the substances produced by CIEAV-62 (RS-CIEAV-62) stain, CIEAV-62 stain grown over its own excretions or secretions (CIEAV-62), of *Rhizoctonia solani* grown over the substances produced from CIEAV-52 strain (RS-CIEAV-52) and CIEAV-52 strain grown over its own excretions or secretions (CIEAV-52).

From the results obtained until this moment, strains CIEAV-30, CIEAV-40 and CIEAV-62 were identified as those with better biological control for most of pathogens tested, that is why they were deposited on Jan. 2, 2002, at the American Type Culture Collection (ATCC), located at 10801 University Boulevard, Manassas, VA. 20110, U.S.A., as International Deposit Authority of Budapest Treaty for International Recognition of Microorganisms Deposit for Purposes of Patent Proceedings, with deposit numbers PTA-3950, PTA-3951 and PTA-3952, respectively. The deposit strains were selected from a Trichoderma strain and collected by process of the present Invention and have been identified as having the capability to control a great number of pathogen variants in wide ranges of pH and temperature. Furthermore, strains CIEAV-30 (ATCC deposit No. PTA 3950) and CIEAV-40 (ATCC deposit No. PTA 3951) were subjected to measurement in planta step to determine its performance with respect to settlement and/or progress of disease in planta by green house assays.

Experiments were done using chili plantelets in 5 replica, using plastic pots with 1 kg of a weight proportion blend of 50% turf and 50% vermiculite, using 5 plants for each experimental replica, which was repeated 2 times. Temperature was held between 27 and 30° C. and was dairy watered. *Trichoderma* spp strains were added to the substrate as a spore slurry ($1 \times 10^8$ spores/kg substrate) while one thousand zoospores obtained in vitro from *Phytophtora capsici* were used to infest soil in the area of the root's neck. Results from these experiments showed death caused by *P. Capsici* at 100% when *Trichoderma*, as a control, was not applied (pathogen control); 40% when CIEAV-30 strain was applied and 0% when CIEAV-40 strain was used. The results also can be analyzed from table 5.

TABLE 5

Greenhouse test with identified *Trichoderma* strains applied to soil and seed

| Trichoderma sp. strain | DAY 3 | | DAY 6 | | DAY 9 | | DAY 12 | | DAY 15 | | Dead Plants % |
|---|---|---|---|---|---|---|---|---|---|---|---|
| | N | M | N | M | N | M | N | M | N | M | |
| CIEAV-30 | 2 | 0 | 2 | 2 | 2 | 2 | 2 | 2 | 2 | 2 | 40 |
| CIEAV-40 | 0 | 0 | 0 | 0 | 0 | 0 | 0 | 0 | 0 | 0 | 0 |
| Pathogen control | 1 | 0 | 5 | 5 | 5 | 5 | 5 | 5 | 5 | 5 | 100 |
| Health control | 0 | 0 | 0 | 0 | 0 | 0 | 0 | 0 | 0 | 0 | 0 |

N = number of plants with necrosis;
M = number of plant deaths

Likewise, CIEAV-30, CIEAV-40 and CIEAV-62 strains were tested in regard to each other compatibility through experiments of direct confrontation, according to table 6, wherein it can be see that strains are acceptably compatible to each other, reason why they can be used in combination to obtain a suitable biological control. Table 6 shows an evaluation in scale from 0 to 9, where 0 is totally compatible and 9 is totally incompatible.

TABLE 6

Compatibility Test Between Selected Strains

| STRAIN | CIEAV-30 | CIEAV-40 | CIEAV-62 |
|---|---|---|---|
| CIEAV-30 | 0 | 4 | 6 |
| CIEAV-40 | | 0 | 1 |
| CIEAV-62 | | | 0 |

Likewise, it can be seen that the best result on compatibility was obtained using together CIEAV-62 and CIEAV-40 strains, although all strains can growth together without the presence of cellular death from the other strains indicated by brown coloration.

For a better understanding of compatibility analysis, table 7 shows the evaluation criteria to evaluate the compatibility between strains, used for the evaluations shown in table 6.

TABLE 7

Evaluation Criteria to Determine Compatibility between Strains

| Value | Criteria |
|---|---|
| 0 | It does not exist growth inhibition at distance by any strain, uniform contact line and there is no over-growth, without pigmentation at contact area, sporulation on normal cyclic patterns |
| 1 | It does not exist growth inhibition at distance by any strain, non-uniform contact line, without pigmentation at contact area, sporulation on normal cyclic patterns |
| 2 | It does not exist growth inhibition at distance by any strain, non-uniform contact line, without pigmentation at contact area, partial sporulation at contact area |
| 3 | It does not exist growth inhibition at distance by any strain, non-uniform contact line, without pigmentation at contact area, partial sporulation at contact area |

TABLE 7-continued

Evaluation Criteria to Determine Compatibility between Strains

| Value | Criteria |
|---|---|
| 4 | It does not exist growth inhibition at distance by any strain, non-uniform contact line, without pigmentation at contact area, discontinuous sporulation |
| 5 | It does not exist growth inhibition at distance by any strain, one strain shows a light initial over-growing over the other strain but it never over-growth more than 3 mm, without pigmentation at contact area, discontinuous sporulation |
| 6 | It does not exist growth inhibition at distance by any strain, one strain shows a light initial over-growing over the other strain but it never over-growth more than 6 mm, without pigmentation at contact area, discontinuous sporulation |
| 7 | It does not exist growth inhibition at distance by any strain, one strain shows a light initial over-growing over the other strain but it never over-growth more than 6 mm, with brown pigmentation indicating cellular death at contact area, limited sporulation |
| 8 | Growth inhibition at distance by one of the strains, one strain over-growth over the other strain more than 6 mm, with brown pigmentation indicating cellular death at contact area |
| 9 | Growth inhibition at distance by one of the strains, one strain over-growth completely over the other strain, with few air-borne mycelium at over-growth and brown pigmentation indicating cellular death at contact area |

According to the aforementioned, it can be seen that the process of the present invention has been thought to efficiently select stains of *Thricoderma*, such as CIEAV-30 (deposit ATCC No. PTA-3950), CIEAV-40 (deposit ATCC No. PTA-3951) and CIEAV-62 (deposit ATCC No. PTA-3952) with the desired biological control activity with an optimal performance in different conditions of pH and temperature and with high compatibility to each other when combining, and it would be obvious to any expert in the art that are possible numerous modifications thereto, as can be the use of different genetic-molecular markers, or culture media or additional growth measurement forms to those illustrated in the present description.

Therefore, the invention shall not be considered as restricted but for the state of the art and for the true scope of the appended claims, interpreted according to the present detailed description of the invention.

What is claimed is:

1. A biologically pure culture of *Trichoderma* CIEAV-40 strain (ATCC Deposit No. PTA-3951) having a high capacity of biological control in a wide range of phytopathogenic fungus under several different environmental conditions.

2. The biologically pure *Trichoderma* CIEAV-40 strain (ATCC Deposit No. PTA-3951) of claim 1, wherein the phytopathogenic fungus are *Fusarium* sp., *Rhizoctonia* sp., *Phytophthora* sp., *Botrytis cinerea* and *Colletotrichum* sp.

3. A biocontrol composition comprising an effective amount of a biologically pure culture of *Trichoderma* CIEAV-40 strain (ATCC Deposit No. PTA-3951).

4. The biocontrol composition according to claim 3, further including a biologically pure culture of *Trichoderma* CIEAV-30 strain (ATCC Deposit No. PTA-3950).

5. The biocontrol composition according to claim 3, further including a biologically pure culture of *Trichoderma* CIEAV-62 strain (ATCC Deposit No. PTA-3952).

6. The biocontrol composition according to claim 3, further including a biologically pure culture of *Trichoderma* CIEAV-30 strain (ATCC Deposit No. PTA-3950) and a biologically pure culture of *Trichoderma* CIEAV-62 strain (ATCC Deposit No. PTA-3952).

* * * * *